US00PP11495P

United States Patent [19]

Ito et al.

[11] Patent Number: Plant 11,495

[45] Date of Patent: Aug. 29, 2000

[54] ZOYSIA GRASS PLANT NAMED 'SS-300'

[75] Inventors: Minoru Ito; Roberto Guerra Amaral Gurgel, both of Itapetininga, Brazil

[73] Assignee: Sod Solutions, Inc., Mt. Pleasant, S.C.

[21] Appl. No.: 09/028,031

[22] Filed: Feb. 24, 1998

[51] Int. Cl.[7] ..... A01H 5/00

[52] U.S. Cl. ..... Plt./390

[58] Field of Search ..... Plt./390, 388

[56] References Cited

U.S. PATENT DOCUMENTS

| | | | |
|---|---|---|---|
| P.P. 5,845 | 12/1986 | Youngner | Plt./390 |
| P.P. 6,345 | 10/1988 | Whiting | Plt./390 |
| P.P. 6,516 | 1/1989 | Whiting | Plt./390 |
| P.P. 6,529 | 1/1989 | Pursley | Plt./390 |
| P.P. 7,074 | 12/1989 | Whiting | Plt./390 |
| P.P. 8,553 | 1/1994 | Staton | Plt./390 |
| P.P. 9,089 | 3/1995 | Yamagishi et al. | Plt./390 |
| P.P. 9,127 | 5/1995 | Gibeault et al. | Plt./390 |
| P.P. 9,135 | 5/1995 | Gibeault et al. | Plt./390 |
| P.P. 10,187 | 1/1998 | Yaneshita et al. | Plt./390 |
| P.P. 10,636 | 10/1998 | Engelke | Plt./390 |
| P.P. 10,778 | 2/1999 | Engelke | Plt./390 |
| 5,413,909 | 5/1995 | Bassam et al. | 435/6 |
| 5,643,479 | 7/1997 | Lloyd et al. | 219/137 |

OTHER PUBLICATIONS

Caetano–Anolles et al. "DNA Amplification Fingerprinting Using . . . " Jun. 1991 Bio/Technology vol. 9 P 553.

Bassam and Bentley "Electrophoresis of Polyester–Backed Polyacrylamide Gels" BioTechniques 19:568 Oct. 1995.

Bassam et al. "Fast and Sensitive Silver Staining of DNA in Polyacrylamide Gels" Analytical Biochemistry 196:80 1991.

*Primary Examiner*—Howard J. Locker
*Assistant Examiner*—Wendy A. Baker
*Attorney, Agent, or Firm*—Myers Bigel Sibley & Sajovec

[57] ABSTRACT

A new and distinct variety of *Zoysia japonica* turfgrass, called 'SS-300', is characterized by a short, narrow leaf blade, compared to other varieties of *Zoysia japonica*. The growth habit is low and compact. 'SS-300' has a rapid establishmentrate.

9 Drawing Sheets

BACKGROUND OF THE INVENTION

The present invention relates to a new and distinct variety of a perennial Zoysia grass, discovered on a Brazilian turf farm in the state of São Paolo during a routine field inspection. The grass was found in a production field of a common Brazilian grass known as 'Wild Zoysia' (unpatented). The new grass is believed to be a sport of 'Wild Zoysia' due to its color, and its smaller size and shorter node length compared to 'Wild Zoysia'. The novel grass, termed 'SS-300', was propagated asexually in the state of São Paolo, Brazil. 'SS-300' is a distinct, asexually propagated variety of Zoysia grass. 'SS-300' is the varietal designation of this new grass. The name 'SS-300' may also designate this plant in commerce.

SUMMARY OF THE INVENTION

'SS-300' is a distinctive Zoysia grass, with a low, compact growth habit. It is characterized by the combination of its color, compact growth habit, and small leaf blade length and width.

BRIEF DESCRIPTION OF THE FIGURES

FIG. 1 provides a comparison of stolons of 'SS-300' and 'SS-500'; a metric scale is included to establish size. 'SS-500' is another new variety of Zoysia grass, and is the subject of co-pending U.S. Plant patent application Ser. No. 09/031,492.

FIG. 2 provides a comparison of 'SS-300', 'SS-500', cultivar 'Meyer', and cultivar 'El Toro'. A metric scale is included to establish size.

FIG. 3 provides a comparison of the 'SS-500' (top) and 'SS-300' (bottom) cultivars.

FIG. 4 shows the seedhead of 'SS-300'.

FIG. 5 shows the rapid runner growth of 'SS-300' at two to three months after planting.

FIG. 6 demonstrates the grey-purple stem color of the 'SS-300' cultivar.

FIG. 7 is a close-up view of 'SS-300' showing the grey-purple stem color.

FIG. 8 shows the rapid growth of 'SS-300'. The grass was sprigged in the center area and plugged in the outlying areas shown in the photograph.

DETAILED DESCRIPTION OF THE VARIETY

Figure 9:
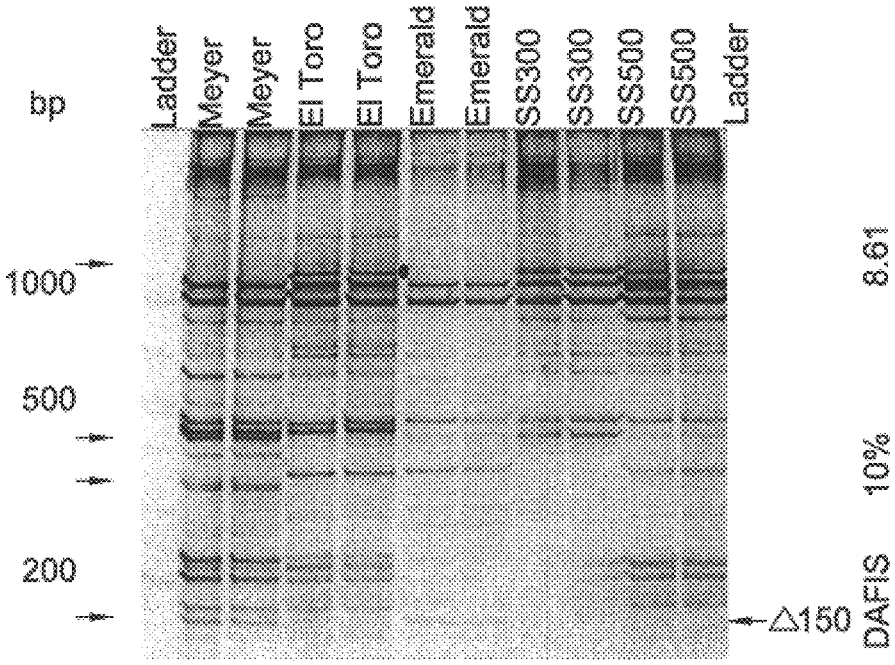
FIG. 9 is a gel showing DNA fingerprint analysis of 'SS-300' in comparison to other varieties of zoyziagrass using primer 8.6i. M=molecular size markers in base pairs. Areas of distinct DNA amplification differences are indicated by small arrows.

The following is a detailed description of the new Zoysia grass variety known as 'SS-300', based upon observations of the plant grown in plug trays and field plots. Color notations are based on *The Royal Horticultural Society Colour Chart*, The Royal Horticultural Society, London.

'SS-300' is a perennial, vegetatively propagated Zoysia grass, believed to be a variety of *Zoysia japonica*. The parent of 'SS-300' is believed to be a native Brazilian variety of *Zoysia japonica*, commonly known as 'Wild Zoysia'. 'SS-300' is a narrow-bladed and low-growing grass, which is unusual for *Zoysia japonica*, which grasses are usually medium to wide-bladed and are larger than 'SS-300' in most respects. Applicants have asexually propagated 'SS-300' by means of stolons and rhizomes. Applicants have discovered the novelty and distinctness of 'SS-300' compared to other varieties of Zoysia.

The leaf blade width and length of 'SS-300' are shorter than 'El Toro' Zoysia (U.S. Plant Pat. No. 5,845) and other comparable types of Zoysia. 'SS-300' has a low and compact growth habit, few seedheads, and shorter and finer leaf blades than 'Wild Zoysia', 'El Toro' or 'Meyer' (unpatented) varieties. Further testing comparing 'SS-300' to variety 'El Toro' (a standard for rapid growth of Zoysia) demonstrates that 'SS-300' can exhibit complete coverage within seven to eight months after planting, compared to 'El Toro' which takes nine to twelve months under similar conditions. Each variety was planted in 8'×8' plots using 4-inch prerooted grass plugs planted 12-inches on center to determine coverage rates.

'SS-300' is characterized by its narrow, short leaf blade; low compact growth habit, and other characteristics described herein. 'SS-300' has a rapid establishment rate, and exhibits drought tolerance and good tolerance to the herbicides MSMA and 2-4-D.

COLOR, DIMENSIONS AND GROWTH HABIT

'SS-300' was discovered on a Brazilian turf farm in a production field of a common Brazilian grass known as 'Wild Zoysia'. The new grass was initially believed to be an 'off-type' or sport of 'Wild Zoysia' due to its color and its smaller size and shorter node length (compared to 'Wild Zoysia'). 'SS-300' exhibits a low and compact growth habit and relatively small leaf width and length, compared to other Zoysia grasses. It has a consistent upright habit, forming an attractive turf. 'SS-300' is very low growing during the initial stage of coverage and remains low after the grass becomes established. Once established, 'SS-300' is a compact, tightly woven grass that remains low to the ground during all stages of growth. The growth and morphology of 'SS-300' is further characterized in Table I, which presents data regarding blade width, blade length, internode length, stolon width, and spike length for 'SS-300' in comparison with other varieties of Zoysia.

TABLE I

| | Length and Width Data | | | | |
|---|---|---|---|---|---|
| | Blade Width (mm) | Blade Length (mm) | Internode Length (mm) | Stolon Width (mm) | Spike Length (mm) |
| 'SS-300' | 1.9–2.3 | 30–40 | 18–25 | 1.0–1.5 | 16–18 |
| 'SS-500' | 4.7–5.5 | 120–140 | 30–35 | 2.0–2.3 | 30–40 |
| 'El Toro' | 3.0–3.2 | 42–47 | 23–27 | 1.4–1.5 | 27–30 |
| 'Meyer' | 3.1–3.6 | 39–42 | 34–38 | 1.5–1.8 | 24–28 |
| 'Emerald'* | 0.5–1.4 | 20–30 | 10–15 | 0.8–1.2 | 12–14 |

*unpatented
Reference; Test plots located at Elsberry Greenhouse in Ruskin, FL.
Reference: Test plots located at Bethel Farms in Arcadia, FL.
8' × 8' plots
Plugged by Elsberry Greenhouse in Ruskin, FL on 2/03/98.
Plugged by Bethel Farms in Arcadia, FL on 2/18/99.
Material attained by special permit USDA Quarantine Lab, Beltsville, MD.

'SS-300' spreads by means of stolons, rhizomes and tillers to form a tight compact groundcover. The stolons are grey-purple in color (183B). Stolons are about 1–1.5 millimeters in width with node lengths about 1.8–2.5 centimeters apart. The nodes of 'SS-300' root adventitiously. New leaves are rolled into bud shoots. Mature leaves are about 1.9–2.5 millimeters in width and about 3–4 centimeters maximum length, and have a dark green color on both upper and lower surfaces corresponding to 137A. The leaves are linked with extremely fine hairs along the outer edge, consistent from the bottom of the leaf to the tapering pointed tip. The culm has the same dark green color (137A) as the leaf blade. The collar is short and continuous. The inflorescence is a single spike at the top of the stem. The anther is white (155D) and the stigmas are green-white (157C) in color. The seed pods have the same dark green color as the leaf (137A). The root system is fine-textured and deep, which is unusual for the species.

'SS-300' demonstrates an extended season as compared with other Zoysia grasses. The 'SS-300' variety exhibits early greening in the Spring and late Fall color retention.

These and other features and characteristics of the 'SS-300' cultivar are apparent from the figures provided herein.

REPRODUCTION

After its initial discovery, 'SS-300' was removed from the production field and transplanted into plug trays for further trials and testing. After several series of cuttings and transplantings were made, 'SS-300' retained the color, size, and node length characteristics that were originally noted. 'SS-300' was then transplanted to field plots for examination.

During examination of 'SS-300' transplanted to field plots, it was noted that 'SS-300' spread at a similar rate to the 'Wild Zoysia' (which has been noted to be faster than both 'Meyer' and 'El Toro' cultivars). Regarding establishment rates, 100% coverage for 'SS-300' has been noted to occur at seven to eight months, compared to typical rates of 12 to 18 months for 'Meyer' Zoysia and nine to 12 months for 'El Toro' Zoysia (U.S. Plant Pat. No. 5,845). More extensive data regarding coverage rates of 'SS-300' in comparison with other Zoysia grasses are presented in Table 2. Other turf characteristics are provided in Table 3 and Table 4.

TABLE 2

| | Percent Coverage Data (%) | | | | | |
|---|---|---|---|---|---|---|
| | Plant # | 30 Days | 60 Days | 90 Days | 120 Days | 150 Days |
| 'SS-300' | 20 | 30 | 40 | 55 | 80 | 95 |
| 'SS-500' | 20 | 35 | 45 | 60 | 85 | 100 |
| 'El Toro' | 20 | 25 | 35 | 50 | 65 | 80 |
| 'Meyer' | 20 | 25 | 30 | 45 | 55 | 70 |
| 'Emerald'* | 20 | 20 | 25 | 35 | 45 | 55 |

*unpatented
Reference; Test plots located at Elsberry Greenhouse in Ruskin, FL.
Reference: Test plots located at Bethel Farms in Arcadia, FL.
8' × 8' plots
Plugged by Elsberry Greenhouse in Ruskin, FL on 2/03/98.
Plugged by Bethel Farms in Arcadia, FL on 2/18/99.
Material attained by special permit USDA Quarantine Lab, Beltsville, MD.

TABLE 3

| | Zoysia Variaty Evaluation | | | | |
|---|---|---|---|---|---|
| | Turf Density | Seedhead Presence | Turf Color | Turf Quality | Disease Presence |
| 'El Toro' | 78.8 | 17.5 | 6.25 | 7.63 | 22.5 |
| 'SS-500' | 92.5 | 18.8 | 6.25 | 8.00 | 15.0 |
| 'Meyer' | 36.3 | 0.0 | 8.13 | 6.25 | 58.5 |
| 'SS-300' | 93.8 | 0.0 | 6.38 | 7.38 | 53.8 |
| 'Emerald' | 17.5 | 0.0 | 7.38 | 6.63 | 58.8 |

TABLE 3-continued

| Zoysia Variaty Evaluation | | | | | |
|---|---|---|---|---|---|
| | Turf Density | Seedhead Presence | Turf Color | Turf Quality | Disease Presence |
| Rating Scale | 0–100% | 0–100% | 1–9<br>1 = light<br>9 = dark | 1–9<br>1 = poor<br>9 = good | 1–100% |
| Rating Date | 7/24/99 | 7/24/99 | 7/24/99 | 7/24/99 | 7/24/99 |

Evaluations performed at Sod Solutions Coastal Research Center, Charleston, South Carolina.

TABLE 4

| Zoysia Variety Evaluation | | | | |
|---|---|---|---|---|
| | Turf Quality | Stolon Regrowth | Plug Mortality | Seedhead Presence |
| 'El Toro' | 7.88 | 29.3 | 0.0 | 30.0 |
| 'SS-500' | 8.00 | 47.0 | 0.0 | 85.0 |
| 'Meyer' | 8.38 | 4.3 | 0.0 | 11.3 |
| 'SS-300' | 8.63 | 150.0 | 0.0 | 1.3 |
| 'Emerald' | 7.00 | 26.5 | 0.3 | 10.0 |
| Rating Scale | 1–9<br>1 = poor<br>9 = good | Number | Percent | 1–100% |
| Rating Date | 5/7/99 | 5/7/99 | 5/7/99 | 5/7/99 |
| | Internode Length | Blade Width | Turf Density | Plug Width |
| 'El Toro' | 26.0 | 3.20 | 7.5 | 15.47 |
| 'SS-500' | 35.0 | 5.23 | 10.0 | 15.90 |
| 'Meyer' | 34.0 | 3.10 | 0.0 | 12.60 |
| 'SS-300' | 19.0 | 2.28 | 11.3 | 15.50 |
| 'Emerald' | 12.0 | 1.20 | 1.3 | 14.22 |
| Rating Scale | mm | mm | 1–100% | cm |
| Rating Date | 5/22/99 | 5/22/99 | 5/22/99 | 5/22/99 |

Evaluations performed at Sod Solutions Coastal Research Center, Charleston, South Carolina.

Sprigs of 'SS-300' establish roots quickly, within three to six days, and the root system is dense and deep. Testing and evaluation determined that the root system of 'SS-300' was more aggressive and more dense, and the roots were finer in diameter, than the comparison 'Wild Zoysia'. Other advantages both physically and morphologically are apparent from the figures provided herein.

'SS-300' can be propagated from sod, plugs, sprigs, stolons, tillers or rhizome pieces. Because 'SS-300' regrows from rhizomes, ribbons or strips of grass are not required to be left in sod fields for successful re-growth after sod harvesting. Seed stability is undetermined at this time, but indications suggest that there is little to no viability.

Asexual propagation of 'SS-300' was carried out in the state of São Paolo, Brazil. Asexual reproduction of 'SS-300' by rhizomes has established that the characteristics and combination of characteristics noted in 'SS-300' are transmitted during succeeding propagations.

ENVIRONMENTAL TOLERANCES

'SS-300' has shown potential for shade tolerance and further shade tolerance tests are underway. The winter hardiness of 'SS-300' is unknown; cold tolerance studies are underway. 'SS-300' has been noted to turn brown after heavy frost, but has good fall color retention and rapid growth rates.

'SS-300' has good drought tolerance, most likely due to the massive and fine-textured root system. After severe wilting, 'SS-300' has been noted to recover with watering.

DISEASE RESISTANCE AND SUSCEPTIBILITY

'SS-300' has resistance to leaf spot and exhibits only limited susceptibility to armyworms as compared with other grasses.

DNA FINGERPRINT ANALYSIS

DNA fingerprint analysis was carried out on 'SS-300' at the University of Tennessee using the methods described in U.S. Pat. No. 5,413,909 and by Caetano-Anolles et al., (1991) *Bio/Technology* 9:553. Cultivar 'SS-500' and standards 'Meyer', 'El Toro', and 'Emerald' (unpatented) were also analyzed. Genomic DNA was isolated from freshly grown material. No evidence of diseased tissue or weeds was detected. Several young blades of grass were ground in liquid nitrogen and DNA extracted. DNA was extracted in duplicate from the supplied samples. The DNA was quantified by fluorimetry, then was diluted and amplified using the standard high primer-low template DNA ratio using DNA amplification fingerprinting (DAF) as described in U.S. Pat. No. 5,413,909 and Caetano-Anolles et al., (1991) *Bio/Technology* 9:553. Stoffel fragment of Taq™ DNA polymerase (Perkin Elmer Corp.) was used to amplify genomic DNA. Primers 8.6i and 10.6e were used.

Amplification occurred in an MJR PT200 thermocycler, using the optimized DAF amplification program DAF15. This program involves fast ramping, high annealing temperatures (55° C.), and an extension step at 72° C. Resulting amplification products were resolved using SUPERGEL™ polyacryalmide gel electrophoresis (Bassam and Bentley, (1995) *Biotechniques* 19:568) and visualized by silver staining as described in U.S. Pat. No. 5,643,479 and Bassam et al., (1991) *Anal. Biochemistry* 196:80.

The DNA was extracted in duplicate from the samples. The DNA was diluted and amplified as described above. Duplicate amplification products were separated by polyacrylamide gel electrophoresis.

Figure 10:
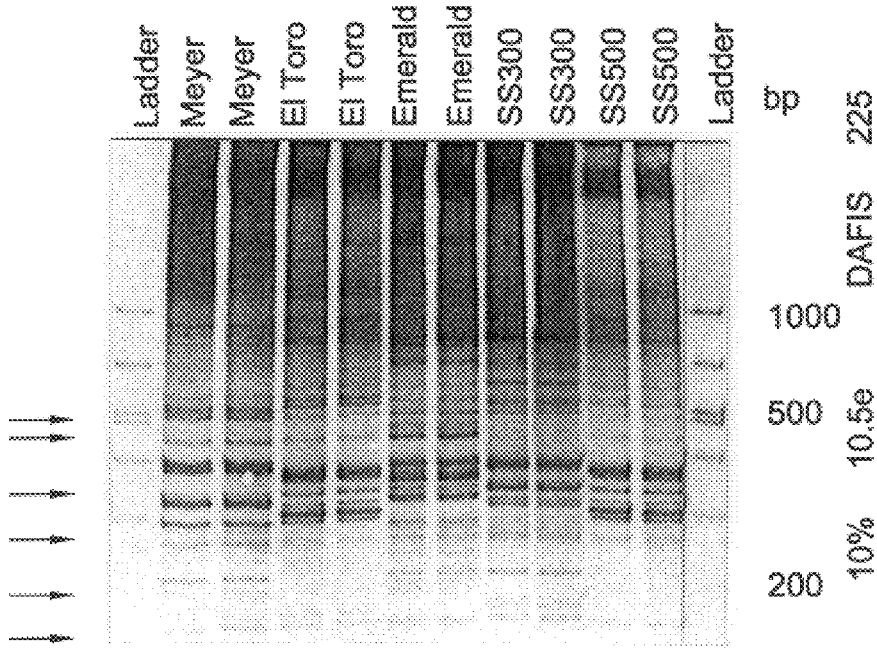
FIG. 10 is a gel showing DNA fingerprint analysis of 'SS-300' in comparison to other varieties of zoyziagrass using primer 10.6e. M=molecular size markers in base pairs. Areas of distinct DNA amplification differences are indicated by small arrows.

Two gels showing the result of DNA analysis are shown in FIG. 9 and FIG. 10, using primer 8.6i or 10.6e, respectively. About 15 major amplification products, seen as strong bands, and about 30 minor ones are commonly seen. The lanes on the sides represent molecular size markers (1000, 700, 500 (doublet), 400, 300, 200 and 100 bp) used to determine the size of the amplification products.

Using primer 8.6i (FIG. 9), several polymorphic bands were seen that distinguish 'SS-300' from the other zoysia cultivars. The primer 8.6i clearly distinguishes the 'Meyer', 'El Toro' and 'Emerald' standards, e.g., in the 400–500 bp region.

The 'SS-300' and 'SS-500' samples are similar to each other, but clearly different. The differences between these two cultivars are even more pronounced with the 10.6e primer (FIG. 10).

The results of the fingerprinting analysis indicated that both 'SS-300' and 'SS-500' are most closely related to 'El Toro'. The 'SS-300' and 'SS-500' varieties appear to be related, but are clearly distinct from each other. Primers 8.6i and 10.6e showed clear polymorphisms for several major bands. Areas of distinct DNA amplification differences are indicated by small arrows in FIG. 9 and FIG. 10.

That which is claimed is:

1. A new and distinct variety of Zoysia grass plant named 'SS-300', substantially as described and illustrated, which has a low compact growth habit, and leaves that are shorter and narrower than Brazilian 'Wild Zoysia' or 'El Toro' Zoysia.

* * * * *